United States Patent
Soe et al.

(10) Patent No.: US 6,200,587 B1
(45) Date of Patent: Mar. 13, 2001

(54) TISSUE SEALANT CONTAINING FIBRINOGEN, THROMBIN AND CARBOXYMETHYL CELLULOSE OR SALT THEREOF

(75) Inventors: Gilbu Soe; Motonori Aoshima; Koichi Takada, all of Tokyo (JP)

(73) Assignee: Hogy Medical Co., Ltd., Tokyo (JP)

( * ) Notice: Subject to any disclaimer, the term of this patent is extended or adjusted under 35 U.S.C. 154(b) by 0 days.

(21) Appl. No.: 09/312,415

(22) Filed: May 14, 1999

(30) Foreign Application Priority Data

May 15, 1998 (JP) .................................................. 10-133290

(51) Int. Cl.[7] .............................. A61F 2/00; A61K 38/00
(52) U.S. Cl. ............................ 424/423; 424/426; 514/21
(58) Field of Search ..................................... 424/423, 426; 514/21

(56) References Cited

U.S. PATENT DOCUMENTS 5,420,250    5/1995   Lontz .
5,631,011  * 5/1997   Wadstrom ............................ 424/400
6,056,970  * 5/2000   Greenawalt et al. ................. 424/426

FOREIGN PATENT DOCUMENTS 63-093717  *  4/1988  (JP) .
8176201       7/1996  (JP) .

OTHER PUBLICATIONS

Turaev et al, Hemostatic Activity and Reabsorbability of Carboxymethyl Cellulose, Khim.–Farm. Zh. 24(8) : 47–51 (1990).*

* cited by examiner

Primary Examiner—Sandra Saucier
(74) Attorney, Agent, or Firm—Burgess, Ryan & Wayne; Milton J. Wayne; William R. Moran

(57) ABSTRACT

A tissue sealant comprising thrombin, fibrinogen, and carboxylmethyl cellulose or an alkali metal or alkali earth metal salt thereof is disclosed. The tissue sealant of the present invention promotes a hemostasis of an injury to a skin surface or a viscus, a healing of an injury, an endothelium formation of a blood vessel, an adhesive activity of animal cells, such as endothelial cells or fibroblasts in vitro, and an adhesion and agglutination of platelets.

11 Claims, 1 Drawing Sheet

TISSUE SEALANT CONTAINING FIBRINOGEN, THROMBIN AND CARBOXYMETHYL CELLULOSE OR SALT THEREOF

BACKGROUND OF THE INVENTION

1. Field of the Invention

The present invention relates to a tissue sealant. More particularly, the present invention relates to a tissue sealant which can seal injuries, reduce loss of blood, maintain a hemostasis, and promote healing of an injured site on a skin surface, organs or the like.

2. Description of the Related Art

Shortly after injuries occur, a healing of injuries, i.e., a recovery of lesions, starts with an adhesion and agglutination of platelets or thrombocytes to the injuries. It is necessary to closely control the consecutively conjugated functions of various cells, and the degradating and regenerating processes. These include a formation of fibrin clots, absorption of blood clots, and epithelialization. The injury-healing comprises a formation of many blood capillaries, active fibroblasts, and collagen fibrils, but is not followed by a formation of a particular skin structure.

A process of healing injuries starts with an adhesion and agglutination of platelets to an injured tissue, and with thromboplastin liberated from the injured cells at the same time. Thromboplastin activates coagulation factors, and finally converts prothrombin to thrombin. By a catalyzing action of thrombin, fibrinopeptides A and B are released from fibrinogen to form fibrin monomers. The monomers are aggregated to form fibrin filaments. Thrombin also activates the blood coagulation factor XIII (the Factor XIII), which catalyzes an isopeptide formation to covalently cross-link fibrin filaments. Then, $\alpha$-antiplasmin is bonded to fibrin filaments by the activated Factor XIII, whereby a degradation of fibrin filaments by plasma components is prevented.

The platelets adhered and agglutinated to the injured site liberate PDGF's. PDGF's include a platelet-derived growth factor (PDGF), a platelet-derived angiogenic factor (PDAF), a transforming growth factor-$\beta$ (TGF-$\beta$) and a platelet factor-4 (PF-4).

PDGF is a mitogen, and stimulates a protein synthesis in cells originating in mesenchyme, such as fibroblastes and smooth muscle cells. PDGF is an amitosis attractant for an endothelial cell.

TGF-$\beta$ is an attractant for a macrophage and monocytes. TGF-$\beta$ stimulates or inhibits various cells, dependent upon the presence or absence of other growth factors. For example, when applied in vivo, TGF-$\beta$ increases a tension-strength of a cured skin of an injury. Further, TGF-$\beta$ stimulates a synthesis of collagen and glucosamine glycan.

A growth factor liberated from the platelet is potentially useful in specifically promoting a healing of injuries and a recovery of tissues. It was experimentally proved that a closure of injuries, growth of blood vessels or the like is facilitated by applying an extrinsic growth factor to an injured site. Therefore, the safest method for a living body is to utilize growth factors liberated from the platelets adhered and agglutinated onto an injured site.

As a composition for sealing an injured site, reducing a loss of blood, and maintaining a hemostasis, a surgical adhesive and tissue sealant containing plasma proteins are known, and used in the sealing of injured sites on a skin surface or intracorporeal organ. Such a sealant generally contains one or more blood coagulation factors and other plasma proteins. For example, European Patent No. 0,068,047 discloses an anhydrous powder material derived from a concentrated plasma fraction containing fibrinogen, fibrinolysis inhibitors, and thrombin or prothrombin. However, the material can be applied only in the form of powder, because blood clots are formed immediately after water is added. Further, AU-A75097/87 discloses a one-component adhesive containing fibrinogen, the Factor XIII, a thrombin inhibitor such as antithrombin III, a prothrombin factor, a calcium ion, and optionally, a plasmin inhibitor. U.S. Pat. Nos. 4,427,650 and 4,427,651 disclose an enriched plasma derivative containing fibrinogen, thrombin and/or plasmin, and fibrinolysis inhibitors, and optionally, other components such as platelet extracts. U.S. Pat. Nos. 4,627,879 and 4,928,603 disclose a cryoprecipitated suspension containing fibrinogen and the Factor XIII, and a use thereof in the preparation of a fibrin glue, or a fibrin adhesive.

The fibrin adhesive is called a fibrin sealant, and was initially formulated for a clinically topical application, and used for controlling bleeding and curing injuries. The fibrin adhesive is prepared from plasma, and an exact composition of a particular fibrin adhesive depends on a particular plasma fraction used as a starting material. Generally, the fibrin adhesive contains a mixture of proteins which can form blood clots when admixed with thrombin. For example, the fibrin adhesive may be prepared by cryoprecipitating plasma, and fractioning the precipitate to obtain a composition which can form a sealant or blood clots when admixed with thrombin or a thrombin activator. The fractionating of plasma components can be carried out by standard methods of purifying proteins, for example, a precipitation with ethanol, polyethylene glycol or ammonium sulfate, an ion-exchange, or a gel filtration chromatography. In general, the fibrin adhesive comprises a fibrinogen concentrate containing fibronectin, the Factor XIII, and the von Willebrand factor, and dried human or bovine thrombin. It is prepared as a lyophilized form, and admixed with calcium chloride shortly before use. After the admixing, the components are aggregated on the tissue surface to form blood clots containing cross-linked fibrins. The Factor XIII is contained in the fibrinogen concentrate, and catalyzes the cross-linking reaction. The fibrin adhesive seals the surfaces of tissues, and prevents air or liquid from leaking, to thereby induce a hemostasis. The fibrin adhesive promotes the healing of an injury by means of functions to stop bleeding and prevent a flow of blood from an injury.

However, such a conventional fibrin adhesive per se does not exhibit a property of curing or healing an injury. Therefore, it is desired to develop a fibrin adhesive which can be applied to an injury on a skin surface or an intracorporeal tissue, and is useful to maintain a hemostasis and enhance a property of curing or healing an injury.

SUMMARY OF THE INVENTION

Accordingly, the object of the present invention is to provide a tissue sealant which can promote a hemostasis and a healing of an injury on a skin or a viscus, an endothelium formation of a blood vessel, a cellular adhesion of animal cells such as endothelial cells or fibroblasts in vitro, and an adhesion and agglutination of platelets. That is, the object of the present invention is to provide a tissue sealant which can promote a healing of an injury, an endothelium formation or a cellular adhesion of animal cells by applying the sealant capable of agglutinating platelets or thrombocytes to an injured tissue, a blood vessel or animal cells such as endothelial cells or fibroblasts cultured in vitro, to maintain a contact of growth factors induced by platelets or thrombocytes with the injured tissue, the blood vessel or animal cells for a long time.

Other objects and advantages will be apparent from the following description.

In accordance with the present invention, there is provided a tissue sealant comprising thrombin, fibrinogen, and carboxylmethyl cellulose or an alkali metal or alkali earth metal salt thereof.

DESCRIPTION OF THE PREFERRED EMBODIMENTS

Figure 1:
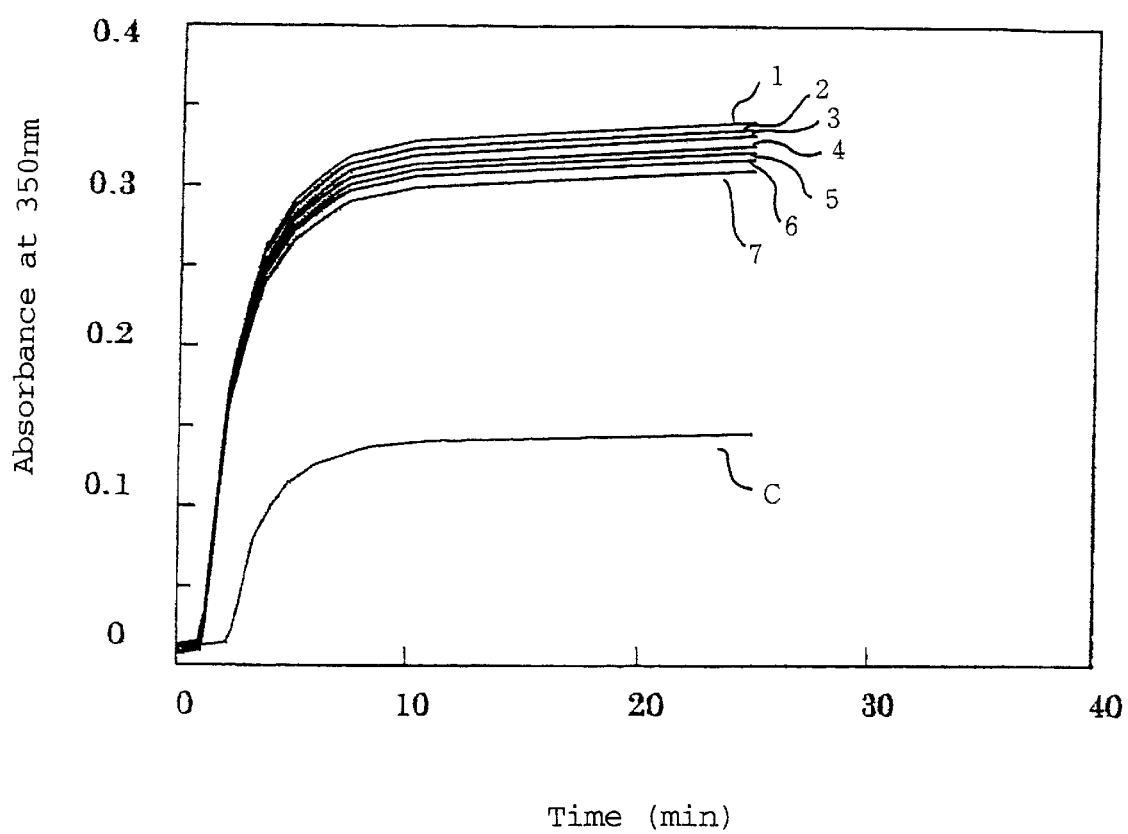
FIG. 1 illustrates an effect of sodium carboxylmethyl cellulose on an aggregation reaction of fibrin monomers.

The tissue sealant according to the present invention may be prepared, for example, by admixing thrombin and carboxylmethyl cellulose or an alkali metal or alkali earth metal salt thereof with fibrinogen prepared from plasma proteins. The tissue sealant may be applied to an injury to form blood clots in situ, and as a result, seal the injury, reduce a loss of blood, and maintain a hemostasis.

A carboxylmethyl cellulose which may be used in the present invention is a polyfunctional carboxylmethyl ether of a cellulose which is etherified with carboxylmethyl groups at a part or all of hydroxy groups, and an alkali metal salt or an alkali earth metal salt thereof (hereinafter sometimes referred to as a carboxylmethyl cellulose salt) is an alkali metal salt or an alkali earth metal salt of the polyfunctional carboxylmethyl ether.

The degree of etherification with carboxylmethyl groups is not particularly limited, but is preferably 0.5 to 1.5, more preferably 0.6 to 0.95, and most preferably 0.6 to 0.8, to ensure an appropriate water-solubility. The position of the hydroxyl group to be etherified is not particularly limited, that is, one or more hydroxy groups at 2-, 3- and/or 6-positions may be etherified.

The average molecular weight of the carboxylmethyl cellulose or the salt thereof is not particularly limited, but is preferably 100 kD to 100000 kD, more preferably 100 kD to 2000 kD, and most preferably 200 kD to 1000 kD. A low molecular weight carboxylmethyl cellulose or the salt thereof may be prepared by etherifying a low molecular weight cellulose, and optionally, converting the etherified cellulose to a salt thereof, or generally, by etherifying a high molecular weight cellulose, and degrading the etherified cellulose before or after an optional conversion to the salt. The degradation may be carried out by a known method, such as an electron ray irradiation or γ-ray irradiation. The degradation by the electron ray irradiation or γ-ray irradiation is preferable, because the product is thus sterilized at the same time.

The content of the alkali metal or alkali earth metal in the carboxylmethyl cellulose salt used in the present invention is not particularly limited, but is preferably 5–13% by weight, more preferably 5–10% by weight, and most preferably 6–8% by weight. The alkali metal is, for example, sodium, potassium or lithium, and the alkali earth metal is, for example, calcium or magnesium. The carboxylmethyl cellulose or the salt thereof used in the present invention may contain one or more alkali metal or alkali earth metal as above.

In the tissue sealant of the present invention, there may be used a fibrinogen and thrombin used in a conventional fibrin sealant or fibrin adhesive. That is, a commercially available fibrinogen, or a fibrinogen prepared by a known method (such as a cryoprecitating method) from plasma may be used. Further, a commercially available thrombin, or a thrombin isolated by a known method (such as an extracting method) from plasma may be used.

The tissue sealant of the present invention may be prepared, for example, by adding a thrombin to a fibrinogen prepared by a cryoprecitation of plasma, and then adding thereto carboxylmethyl cellulose or the salt thereof. The present tissue sealant may be also prepared by adding carboxymethyl cellulose or the salt thereof to a fibrinogen prepared by a cryoprecitation of plasma, and adding thereto a thrombin shortly before use. Further, the present tissue sealant may be also prepared by adding carboxymethyl cellulose or the salt thereof to a commercially available fibrin adhesive, such as a fibrin adhesive from IMMUNO AG (Austria) or BEHRINGWERKE AG (Germany).

During the preparation process of the tissue sealant of the present invention, or before its use, it is preferable to carry out a sterilization or inactivation of pathogenic contaminants, such as viruses. The inactivating method is known to those skilled in the art, for example, but not limited to, a treatment with a solvent-detergent.

The composition of the tissue sealant of the present invention is not limited, as long as the objects of the present invention can be achieved. However, a concentration of the total proteins is preferably 5–150 mg/ml, more preferably 7–35 mg/ml, and most preferably 17–28 mg/ml, with respect to the whole tissue sealant. A concentration of fibrinogen is preferably 4–135 mg/ml, more preferably 6–30 mg/ml, and most preferably 15–25 mg/ml, with respect to the whole tissue sealant. A concentration of carboxylmethyl cellulose or the salt thereof varies with the molecular weight or a degree of etherification of the carboxylmethyl cellulose used, or with the content of the salt, but is preferably 1 µg/ml–100 mg/ml, more preferably 100 µg/ml–100 mg/ml, and most preferably 5 mg/ml–20 mg/ml, with respect to the whole tissue sealant. A concentration of thrombin varies with the concentration of fibrinogen used, but is generally 1–100 NIH unit/ml, more preferably 5–50 NIH unit/ml, and most preferably 10–30 NIH unit/ml.

The tissue sealant of the present invention may contain, in addition to fibrinogen, thrombin, and carboxylmethyl cellulose or the salt thereof, for example, one or more compounds capable of accelerating a healing of an injury, one or more compounds capable of strengthening, stimulating or mediating biological activities of growth factors derived from platelets or thrombocytes in the tissue sealant, one or more compounds capable of inhibiting or interfering with one or more components in the tissue sealant which components may possibly inhibit or block the biological activities of growth factors derived from platelets or thrombocytes in the tissue sealant, or one or more compounds capable of inhibiting or interfering with one or more components in the tissue sealant, which components may inhibit the activities of carboxylmethyl cellulose or the salt thereof. Among the above compounds, a particular compound, such as the inhibiting compound, will be experimentally determined by a method of examining the biological activities of growth factors derived from platelets or thrombocytes in the tissue sealant.

Specifically, the tissue sealant of the present invention may contain, for example, an antibiotic, activated protein C, heparin, prostacyclin (PGI3), antithrombin III, ADPase, an anticoagulant such as a plasminogen activator, an anti-inflammatory steroid such as dexamethasone, a cardiovascular agent such as a calcium channel-blocking agent, an attractant, and a local anaesthetic such as bupivacaine.

The tissue sealant of the present invention may further contain polyclonal, monoclonal or chimera antibodies, or functional derivatives or fragments thereof. These may be antibodies that inhibit the growth of a smooth muscle or a growth of undesired cells within or around the site where the tissue sealant is applied, such as an antibody to PDGF and/or TGF-β. The antibodies as above are useful under the conditions that an antitumor, antiplatelet or anti-inflammatory activity is required. Generally, any antibodies capable of making an effective or economical improvement by a site-specific delivery can employ the present fibrin adhesive delivery system.

The tissue sealant of the present invention can be applied to an injured lesion in a form suitable for the application purposes. For example, the tissue sealant may be liquid or powder. When a liquid sealant is prepared, water or a buffer may be used as a solvent.

The tissue sealant of the present invention may act as a carrier vehicle which allows one or more growth factors liberated from platelets to reach an injured lesion. Further, the tissue sealant of the present invention has adhesive and adsorbable properties, and can maintain a contact of the sealant with the injured lesion for a time sufficient to ensure that the tissue sealant containing an added carboxylmethyl cellulose promotes a healing of an injury.

The tissue sealant of the present invention may provide a matrix to fill a gap necessary to transfer cell components and cause an induction of a bone in a living human body. Therefore, it is preferable to formulate the sealant from proteins (fibrinogen, the Factor XIII, and so on), enzymes (thrombin, plasmin, and so on), and carboxylmethyl cellulose or the salt thereof in such a manner that a temporary scaffold structure as above remains for as long as possible. Although all of the components in the tissue sealant of the present invention are biodegradable, the sealant preferably provides a nondestructive scaffold during a bone formation so that a shape of a newly forming bone can be determined. As above, one of the problems in an osteoanagenesis operation, that is, a collapse of a soft tissue into a bone non-connective deficit, can be avoided.

The tissue sealant of the present invention may be applied to any injury, that is, any injured tissues in living organisms. The injured tissue may be an intracorporeal tissue, such as an inside wall of a stomach, a fracture, or the like, or a skin surface or the like, and also a soft tissue, such as a spleen, or a hard tissue, such as a bone. The injury may be a lesion, trauma or wound, or one formed by an infection or from a surgical operation.

The tissue sealant of the present invention forms fibrin by the actions of thrombin and fibrinogen when used.

When the present invention is worked, a fibrin adhesive and carboxylmethyl cellulose or the salt thereof are selected in view of a site to which it is to be applied. The composition of the tissue sealant of the present invention is not critical, as long as it acts as a tissue sealant in vivo, and as a medium for a contact of carboxylmethyl cellulose or the salt thereof with an injured tissue or a hemal implant, to thereby promote a healing of an injury or a formation of an endothelium. The fibrin adhesive used as a vehicle for growth factors contains as its components fibrinogen, fibronectin, the Factor XIII, and the von Willebrand factor. The amount of each growth factor added will be experimentally determined by conducting tests at various concentrations and selecting a concentration useful to an intended purpose and a site to which it is to be applied.

EXAMPLES

The present invention will now be further illustrated by, but is by no means limited to, the following Examples.

Preoaration Example 1

Preparation of Low Molecular Weight CMC—Na's

Carboxylmethyl cellulose sodium salts (CMC—Na's) having various molecular weights were prepared by an electron ray irradiation. More particularly, solid sodium carboxymethyl cellulose (the degree of etherification=0.8; the content of sodium=8% by weight) was exposed to electron rays of 20 kGy, 40 kGy, 60 kGy, 80 kGy, or 100 kGy at 10 MeV by a CIRCE-II linear accelerator (CGR-McV). The term "Gy" means gray, a unit of a radiation energy, and 1 Gy corresponds to 1 J/kg.

Non-irradiated or irradiated sodium carboxylmethyl cellulose was dissolved in distilled water, and lyophilized. Then, the lyophilized product was crushed in a mortar, and the resulting powder was used in the determination of molecular weights, and in the following Examples.

The molecular weights were determined as follows:

The powder of non-irradiated or irradiated sodium carboxylmethyl cellulose was dissolved in a 50 mM tris-HCl buffer containing 0.15M NaCl, and applied in a Sepharose CL-6B column equilibrated with the same buffer to carry out a molecular sieve chromatography. Sodium carboxylmethyl cellulose was detected by a phenol-sulfuric acid method. The results are shown in Table 1.

TABLE 1

| | Non-irradiated | Irradiated with electron rays | | | | |
|---|---|---|---|---|---|---|
| | | 20 kGy | 40 kGy | 60 kGy | 80 kGy | 100 kGy |
| Molecular weight | 2000 kD | 1000 kD | 800 kD | 600 kD | 400 kD | 200 kD |

Table 1 shows that sodium carboxylmethyl cellulose can be degraded to a low molecular weight compound by an irradiation of electron rays.

Preparation Example 2

Preparation of Tissue Sealant

Human whole blood was centrifuged to obtain plasma. The resulting plasma was then frozen at −80° C. for at least 12 hours. The frozen plasma was then thawed slowly at 4° C., and the centrifuging tube was centrifuged again in a refrigerated centrifuge. The supernatant was carefully decanted. The cryoprecipitate was resuspended in the remaining plasma by tapping the tube. To the resulting suspension of the cryoprecipitate, a commercially available thrombin was added to prepare a fibrin adhesive, and then the powdery non-irradiated or irradiated sodium carboxylmethyl cellulose (CMC—Na) prepared in Preparation Example 1 at a concentration of 10 mg/ml was added to prepare a tissue sealant. The resulting tissue sealant, i.e., a fibrin adhesive containing added CMC—Na, contained 0.1 mg/ml total proteins, 0.02 NIH unit/ml thrombin, and 4 mg/ml fibrinogen.

Reference Example 1

Activity for Aggregating Fibrin Monomers

A powdery non-irradiated or irradiated sodium carboxylmethyl cellulose (CMC—Na) prepared in Preparation Example 1 was dissolved in a 20 mM imidazole buffer containing 0.15M NaCl, to the concentration of 10 mg/ml.

To 0.5 ml of the resulting solution was added 20 μl of a fibrin monomer solution (A280 nm=6) prepared by dissolving fibrin monomers in 20 mM acetic acid, and admixed for 5 seconds. Thereafter, the mixture was poured into a quartz cell having an optical path of 1 cm. After 20 seconds of adding fibrin monomers, an absorbance at 350 nm was measured every 30 seconds for 25 minutes. As a control test, the same procedure was repeated except that the powdery sodium carboxylmethyl cellulose was not used. The absorbance was measured by an ultraviolet-visible light spectrophotometer (U-3210; Hitachi Ltd.). The results are shown in FIG. 1, wherein the curve 1 is the result in the presence of CMC—Na not irradiated with electron rays, the curve 2 is the result in the presence of CMC—Na irradiated with 10 kGy, the curve 3 is the result in the presence of CMC—Na irradiated with 20 kGy, the curve 4 is the result in the presence of CMC—Na irradiated with 40 kGy, the curve 5 is the result in the presence of CMC—Na irradiated with 60 kGy, the curve 6 is the result in the presence of CMC—Na irradiated with 80 kGy, and curve 7 is the result in the presence of CMC—Na irradiated with 100 kGy). Further, the curve C shows the result of the control test.

FIG. 1 shows that sodium carboxylmethyl cellulose remarkably accelerates the aggregation of fibrin monomers, independently of the irradiation of electron rays, i.e., in its wide molecular weight range.

Example 1

Growth of Human Endothelial Cells of Umbilical Vein in the Tissue Sealant

A growth of human endothelial cells of an umbilical vein in the tissue sealant (containing 10 mg/ml sodium carboxylmethyl cellulose having a molecular weight of 200 kD) prepared in Preparation Example 2 was confirmed. Human endothelial cells of umbilical vein were embedded at a density of $1 \times 10^6$ cells/ml in the tissue sealant. A culture medium used was M299 (Sigma Chemical) containing 10% fetal bovine serum, 10 μg/ml streptomycin, 100U/ml penicillin, 1 mg/ml acid fibroblast growth factor, and 10U/ml heparin.

The cells embedded in the tissue sealant became slender and multipodial within 6 hours, and when the cells came into contact with each other, cell-networks were formed. The growth was maintained for at least 3 days. As a control test, the same procedure as above was repeated except that a tissue sealant prepared as in Preparation Example 2 without sodium carboxylmethyl cellulose was used. In the control test, the cells were spherical, and cell-networks were not formed. This condition continued for at least 3 days.

As above, it is manifest that when sodium carboxylmethyl cellulose is added, endothelial cells are grown.

Example 2

Injury-healing in Vivo

An effect of the fibrin adhesive with added CMC—Na on a healing of injuries in diabetic mice was examined. Two injuries (about 1 cm×about 1 cm; depth=about 6 mm) were made on a back skin of each of 6 mice. The tissue sealant (containing 10 mg/ml sodium carboxylmethyl cellulose having a molecular weight of 200 kD) prepared in Preparation Example 2 was filled to one of the injuries, whereas a tissue sealant prepared as in Preparation Example 2 without sodium carboxylmethyl cellulose (a fibrin adhesive without CMC—Na) was filled to the other injury. After 9 days, pathological sections (thickness=5 μm) were taken from the two injuries and a normal skin without an injury (for control), and stained with hematoxylin and eosin. The degree of a healing of injuries in the sections was evaluated by three analysts through a blind test. Specifically, the degree of a healing of injuries was evaluated in 16 stages (from o point meaning not healed to 15 point meaning a complete healing) with respect to a deposition of collagen, a regeneration of epithelial cells, a thickness of particulate tissues, a density of inflamed cells, and fibroblasts and capillary vessels. The results are shown in Table 2.

TABLE 2

| Mice Nos. | Normal Skin | Fibrin adhesive without CMC-Na | Fibrin adhesive with CMC-Na |
|---|---|---|---|
| 1 | 14 | 3 | 14 |
| 2 | 15 | 2 | 13 |
| 3 | 15 | 4 | 15 |
| 4 | 15 | 4 | 14 |
| 5 | 15 | 0 | 13 |
| 6 | 15 | 1 | 14 |

Table 2 shows that the sections taken from their treated with the fibrin adhesive not containing CMC—Na constantly made low scores, whereas the sections taken from the normal skins and the injuries treated with the fibrin adhesive containing CMC—Na recorded high scores.

Example 3

Healing Effect of Injuries

An injury-healing effect of a fibrin adhesive containing sodium carboxylmethyl cellulose was examined.

The livers of 10 mice were exposed by an abdominal operation, and two square portions (1 cm×1 cm, each) were cut from the surface of each liver to make wounded portions. One injury was covered with the tissue sealant (containing 10 mg/ml sodium carboxylmethyl cellulose having a molecular weight of 200 kD) prepared in Preparation Example 2, whereas other injury was covered with a tissue sealant prepared as in Preparation Example 2 without sodium carboxylmethyl cellulose (a fibrin adhesive without CMC—Na). Then, the abdominal region was closed. After one month, the liver was exposed again, and a pathological section was prepared from the portion covered with the fibrin sealant. The degree of healing was evaluated.

It was revealed that the injuries treated with the fibrin adhesive containing sodium carboxylmethyl cellulose were completed cured, and no inflammation was observed, whereas many leukocytes and very severe inflammation were observed in the injuries treated with the fibrin adhesive not containing sodium carboxylmethyl cellulose.

Example 4

Adhering and Agglutinating Properties of Platelets

The adhering and agglutinating properties of platelets on the fibrin adhesive containing sodium carboxylmethyl cellulose were examined. A sheet of the tissue sealant (containing 10 mg/ml sodium carboxylmethyl cellulose having a molecular weight of 200 kD) prepared in Preparation Example 2, and a sheet of the tissue sealant prepared as in Preparation Example 2 without sodium carboxylmethyl cellulose (a fibrin adhesive without CMC—Na) were placed on a 96-well titer plate, and then a human whole blood sample was filled thereon. The adhesion was measured by a method of Haverstick DM, et al. (Blood, 66:946, 1985).

It was revealed that in the tissue sealant not containing sodium carboxylmethyl cellulose, an adhesion and aggulutination of platelets were rarely observed, whereas in the tissue sealant containing sodium carboxylmethyl cellulose, a considerable number of platelets were adhered and agglutinated. Further, growth factors such as (PDGF, TGF-β and the like) derived from platelets were detected in a supernatant obtained by filling a human whole blood sample on the tissue sealant containing sodium carboxylmethyl cellulose, and allowing to stand at 37° C. for 24 hours.

As above, the tissue sealant containing carboxylmethyl cellulose according to the present invention can maintain a contact with an injury or cell cultured in vitro for a long time, and promote a brief contact with platelets.

The tissue sealant of the present invention can be applied directly to injured tissues by any means, for example, coated over an injury on a skin surface. Further, the tissue sealant of the present invention can be applied directly to an intracorporeal injury during a surgical operation, to a bone or the like.

The tissue sealant of the present invention is useful for promoting a healing of an injury difficult to cure, such as an injury to a diabetic person, and is particularly useful as a medium allowing one or more growth factors liberated from platelets to reach an injured lesion by an action of adhering and agglutinating platelets, and then maintain a contact of an intracorporeal injury with growth factors for a long time. For example, the tissue sealant of the present invention may be used to accelerate or promote a healing of an intracorporeal injury, such as a fracture site or a gastric ulcer.

The tissue sealant of the present invention is biodegradable, and able to be assimilated into a tissue. Further, it allows growth factors to come into contact with the receptors thereof for a long time, and permits a production of potent biological effects.

In the tissue sealant of the present invention, it is possible to reduce the concentrations of total proteins and fibrinogen in comparison with a conventional sealant. Due to the low concentration, animal cells can move in, pass through, and grow in the tissue sealant of the present invention, and therefore, it can assist a strengthening of adjacent tissues and cells by protease.

Further, the tissue sealant of the present invention may be prepared in a liquid form, and thus can more sufficiently and completely cover a surface than a conventional delivery system. Therefore, the fibrin sealant containing carboxylmethyl cellulose can cover the inside, outside and pores of a blood vessel, and thus reduce a thrombus formation and development of antigenicity.

Although the present invention has been described with reference to specific embodiments, various changes and modifications obvious to those skilled in the art are deemed to be within the spirit, scope, and concept of the invention.

What we claim is:

1. A tissue sealant consisting essentially of thrombin, fibrinogen, and carboxylmethyl cellulose or an alkali metal or alkali earth metal salt thereof.

2. The tissue sealant according to claim 1, wherein the carboxylmethyl cellulose has an average molecular weight of 100 kD to 100,000 kD.

3. The tissue sealant according to claim 1, wherein the carboxylmethyl cellulose has a degree of etherification of 0.5 to 1.5.

4. The tissue sealant according to claim 3, wherein the carboxylmethyl cellulose has a degree of etherification of 0.6 to 0.95.

5. The tissue sealant according to claim 1, which contains an alkali metal or alkali earth metal salt of carboxylmethyl cellulose.

6. The tissue sealant according to claim 5, wherein a content of the alkali metal or alkali earth metal in the salt of carboxymethyl cellulose is 5 to 13% by weight.

7. The tissue sealant according to claim 5, wherein said alkali metal is sodium.

8. A method of promoting the healing of an injury which comprises contacting the site of the injury with a healing promoting amount of the tissue sealant of claim 1.

9. The method of claim 8 wherein the injury is present in a diabetic person.

10. The method of claim 8 wherein the injury is an intracorporeal injury.

11. A tissue sealant consisting essentially of thrombin, fibrinogen and carboxylmethyl cellulose or an alkali metal or alkali earth metal salt thereof, wherein a concentration of total proteins is 5 to 150 mg/ml with respect to the tissue sealant, a concentration of fibrinogen is 4 to 135 mg/ml with respect to the tissue sealant, and a concentration of carboxylmethyl cellulose or an alkali metal or alkali earth metal salt thereof is 1 μg/ml to 100 mg/ml with respect to the tissue sealant.

* * * * *